United States Patent [19]

Bergman et al.

[11] Patent Number: 4,849,534

[45] Date of Patent: Jul. 18, 1989

[54] HYDRIDOMETHYL IRIDIUM COMPLEX

[76] Inventors: Robert G. Bergman; J. Michael Buchanan; Jeffrey M. Stryker; Michael J. Wax, all of P.O. Box 7141, San Francisco, Calif. 94120-7141

[21] Appl. No.: 703,641

[22] Filed: Feb. 21, 1985

[51] Int. Cl.$^4$ .............................................. C07F 15/00
[52] U.S. Cl. ....................................... 556/23; 556/22; 570/235
[58] Field of Search .................................. 556/22, 23

[56] References Cited

U.S. PATENT DOCUMENTS 3,458,547  7/1969  Coffey ................................. 556/23
3,579,551  5/1971  Craddock et al. ................... 556/22

OTHER PUBLICATIONS

Jones, W. D. et al., "Alkane Carbon–Hydrogen Bond Activation by Homogeneous Rhodium(I) Compounds", Organometallics 1983 2, pp. 562–563.
Janowicz, A. H. et al., "Activation of C–H Bonds in Saturated Hydrocarbons . . . and Functionalization of the Metal-Bound Alkyl Groups", J. Am. Chem. Soc., 1983, 105, 3929–3939.
Janowicz, A. H. et al., "C–H Activation in Completely Saturated Hydrocarbons: Direct Observation of M+R–H→M(R)(H)", J. Am. Chem. Soc. 1982, 104, 352–354.
Bergman, R. G. "Activation of Alkanes with Organotransition Metal Complexes", Science, Mar. 2, 1984, vol. 223, pp. 902–908.
Janowicz, A. H. et al., "Oxidative Addition of Soluble Iridium and Rhodium Complexes to Carbon–Hydrogen Bonds in Methane and Higher Alkanes", Pure & Appl. Chem., vol. 56, No. 1, pp. 13–23, 1984.
Wax, M. J. et al., "Reversible C–H Insertion . . . and Thermally Activating Methane", J. Am. Chem. Soc. 1984, 106, 1121.
Janowicz, A. H. et al., "Oxidative Addition of Soluble Iridium and Rhodium Complexes to Carbon–Hydrogen Bonds in Alkanes (1)"-First IUCCP Symposium 1983.
Janowicz, A. H. Ph.D. Thesis, "A Mechanistic Study . . . Hydrogenolysis of M–C Bonds / C–H Bond Activation of Saturated Hydrocarbons", May 1982.
Periana, R. A. et al., "Rapid Intramolecular Rearrangement . . . Cationic Rhodium π-Allyl Complex", J. Am. Chem. Soc. 1984, 106, pp. 7272–7273.
Periana, R. A. et al., "Oxidative Addition of Rhodium . . . and Alkyl Group Functionalization", Organometallics, 1984, 3, pp. 508–516.
Hoyano, J. K. et al., "Oxidative Addition of the Carbon–Hydrogen Bonds . . . Photochemically Generated Iridium(I) Complex", J. Am. Chem. Soc. 1982, 104, pp. 3723–3725.
Jones, W. D. et al., "Kinetics and Thermodynamics of Intra- and Intermolecular Carbon–Hydrogen Bond Activation", J. Am. Chem. Soc. 1985, 107, 620–631.
Periana, R. A. et al., "Oxidative Addition and Rhodium to Alkane C–H Bonds: Enhancement in Selectivity and Alkyl Group Functionalization", Organometallics, 1984, 3, pp. 508–510.

*Primary Examiner*—Patrick P. Garvin
*Assistant Examiner*—George R. Fourson
*Attorney, Agent, or Firm*—S. R. La Paglia; T. G. De Jonghe; Q. T. Dickinson

[57] ABSTRACT

A process for functionalizing methane comprising:
(a) reacting methane with a hydridoalkyl metal complex of the formula:

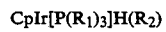

$$CpIr[P(R_1)_3]H(R_2)$$

wherein Cp represents a cyclopentadienyl or alkylcyclopentadienyl radical having from 1 to 5 carbon atoms; Ir represents an iridium atom;
P represents a phosphorus atom;
$R_1$ represents an alkyl group;
$R_2$ represents an alkyl group having at least two carbon atoms; and
H represents a hydrogen atom, in the presence of a liquid alkane $R_3H$ having at least three carbon atoms to form a hydridomethyl complex of the formula:

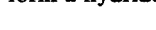

$$CpIr[P(R_1)_3]HMe$$

where Me represents a methyl radical.
(b) reacting said hydridomethyl complex with an organic halogenating agent such as a tetrahalomethane or a haloform of the formulas:

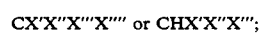

$$CX'X''X'''X'''' \text{ or } CHX'X''X''';$$

wherein X', X'', X''', and X'''' represent halogens selected from bromine, iodine and chlorine, to halomethyl complex of step (a) having the formula:

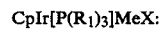

$$CpIr[P(R_1)_3]MeX;$$

(c) reacting said halomethyl complex with a mercuric halide of the formula $HgX_2$ to form a methyl mercuric halide of the formula HgMeX; and
(d) reacting said methyl mercuric halide with a molecular halogen of the formula $X_2$ to form methyl halide.

8 Claims, No Drawings

HYDRIDOMETHYL IRIDIUM COMPLEX

The invention disclosed herewith arose at the Lawrence Berkeley Laboratory in the course of, or under Contract No. DE-AC03-76SF00098 between the U.S. Department of Energy and the University of California.

FIELD OF THE INVENTION

The present invention relates to functionalizing saturated hydrocarbons, and more particularly relates to functionalizing or enhancing the reactivity of methane by converting it to methyl halide.

BACKGROUND OF THE INVENTION

The large quantity and low reactivity of methane has tantalized organic and organometallic chemists for years. The enormous quantity of methane that is produced at locations remote from natural gas pipelines has stimulated researchers throughout the petroleum industry to search for processes that can convert methane to more reactive and/or more easily transportable materials.

Various approaches to reaction of hydrocarbons have been studied over the years including thermal, chemical and photochemical. Examples of these are set forth in Janowicz and Bergman, J. Am. Chem. Soc. 105, 3929–3939 (1983). Most of these prior methods have consumed large amounts of energy in one form or another and suffered other disadvantages.

Recently it was reported that certain organoiridium complexes are capable of intermolecular oxidative addition to single C—H bonds in saturated hydrocarbons leading to hydridoalkyl iridium complexes which can be used to convert alkanes to alkyl halides. This is reported in, for example, Janowicz and Bergman, J.A.C.S. 104, 352 (1982). While these previously reported procedures have proven effective for a wide variety of alkanes, methane was not reactive under the conditions reported.

OBJECTS OF THE INVENTION

It is a principal object of this invention to provide a method of functionalizing methane.

It is an important object to provide a method of functionalizing methane which can be carried out at relatively mild conditions.

Still another and very important object of this invention is to provide a method which enables starting material to be regenerated and reused.

A further object is to provide methyl-substituted iridium complexes useful in the process for functionalizing methane and a method for producing such complexes.

Additional objects, advantages and novel features of the invention will be set forth in part in the description which follows, and in part will become apparent to those skilled in the art upon examination of the following, or will be learned by practice of the invention. The objects and advantages of the invention may be realized and attained by means of the instrumentalities and combinations particularly pointed out in the appended claims.

SUMMARY OF THE INVENTION

A process for functionalizing methane comprising:
(a) reacting methane with a hydridoalkyl metal complex of the formula:

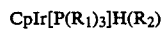
CpIr[P(R$_1$)$_3$]H(R$_2$)

wherein Cp represents a cyclopentadienyl or alkylcyclopentadienyl radical having from 1 to 5 alkyl groups;
Ir represents an iridium atom;
P represents a phosphorus atom;
R$_1$ represents an alkyl group;
R$_2$ represents an alkyl group having at least two carbon atoms; and
H represents a hydrogen atom, in the presence of a liquid alkane R$_3$H having at least three carbon atoms to form a hydridomethyl complex of the formula:

CpIr[P(R$_1$)$_3$]HMe where Me represents a methyl radical.
(b) reacting said hydridomethyl complex with an organic halogenating agent such as a tetrahalomethane or a haloform of the formulas:

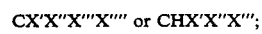
CX'X''X'''X'''' or CHX'X''X''';

wherein X', X'', X''', and X'''' represent halogens selected from bromine, iodine and chlorine, to form the corresponding halomethyl complex of step (a) having the formula:

CpIr[P(R$_1$)$_3$]MeX;

(c) reacting said halomethyl complex with a mercuric halide of the formula HgX$_2$ to form a methyl mercuric halide of the formula HgMeX; and
(d) reacting said methyl mercuric halide with a molecular halogen of the formula X$_2$ to form methyl halide.

DETAILED DESCRIPTION OF THE INVENTION

In brief, a preferred embodiment of the process can be described illustratively in equation form as follows:

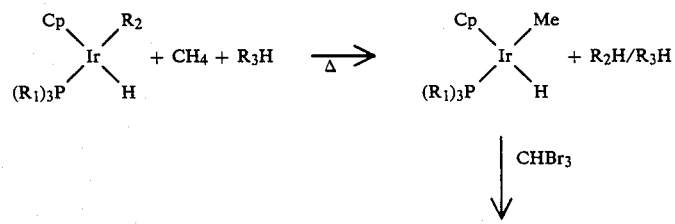

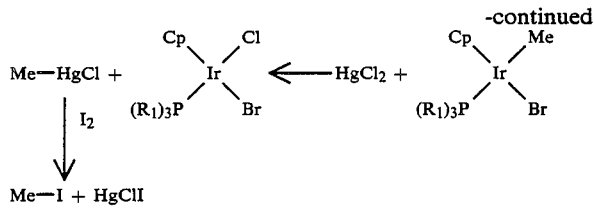

wherein Cp represents a cyclopentadienyl or alkylcyclopentadienyl radical (i.e., a cyclopentadienyl having 1 to 5 substituted alkyl groups) such as a pentaethylated or pentamethylated cyclopentadienyl radical;

$P(R_1)_3$ represents a trialkylated phosphorous radical or a trialkylphosphine radical;

Ir represents an Iridium atom;

H represents a hydrogen atom;

$R_1$ represents an alkyl radical;

$R_2$ represents an alkyl radical having at least 3 carbon atoms;

$R_3$ represents an alkyl radical having at least 3 carbon atoms; and

X represents a halogen atom as defined herein. Preferably $R_1$ is a methyl or ethyl group, $R_2$ has from about 2 to 10 carbon atoms and more preferably is a cyclopentyl or cyclohexyl group and $R_3$ has from about 3 to 10 carbon atoms and more preferably is a cycloheptyl or cyclooctyl group.

An important aspect of this invention is the discovery that, unlike other alkanes, methane is not activated by the dihydride $Cp[P(R_1)_3]IrH_2$ complex in the presence of ultraviolet radiation to form $Cp[P(R_1)_3]IrMeH$. At normal pressures, such low temperatures are required to liquefy methane that the dihydride is insoluble in it. Even inert solvents did not cause the methane to react with the dihydride. For example irradiation of $Cp(PMe_3)IrH_2$ (Cp=pentamethylcyclopentadienyl) in perfluoroalkane solvents (in which it is only slightly soluble) under 4 atmospheres of $CH_4$ gave only decomposition to intractable materials.

We have found that the methane activation can be achieved thermally by heating a hydridoalkyl complex

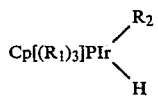

with methane in the presence of a liquid alkane solvent. The hydridomethyl complex, being more stable than the original hydridoalkyl complex or the hydridoalkyl complex potentially formed from the alkane solvent, acts as the "thermodynamic sink" for the system.

DETAILED DESCRIPTION OF PROCESS STEPS

Step (a) $CpIr[P(R_1)_3]H(R_2)+CH_4$

$CpIr[P(R_1)_3]HMe+R_1H$

The alkyl hydridometal complex starting material can be prepared in accordance with the general procedures taught in Janowicz and Bergman "Activation of C—H Bonds in Saturated Hydrocarbons on Photolysis on (h5-C5Me5)(PMe3)-IrH2. Relative Rates of Reaction of the Intermediate with Different Types of C—H Bonds and Functionalization of the Metal-Bound Alkyl Groups" J. Am. Chem. Soc. (1983), 105, pp. 3929–3939 the disclosure of which is incorporated herein by reference in its entirety. It is necessary that both the alkylhydridometal complex starting material and the alkylhydridometal complex which would potentially result from substitution reaction with the alkane solvent be thermally unstable at the reaction conditions of the first step of the process, thus favoring productions of the methylhydridometal complex. $R_2$ and $R_3$ can be the same or different alkyl groups.

The Cp radical can be cyclopentadienyl or alkylcyclopentadienyl (e.g., cyclopentadienyl having 1 to 5 substituted alkyl groups). Preferred are pentamethylcyclopentadienyl or pentaethylcyclopentadienyl. $R_1$ is alkyl, preferably methyl or ethyl or less preferably phenyl. $R_2$ is alkyl having two or more carbon atoms, e.g., 2 to 20 carbon atoms, preferably cyclopentyl or cyclohexyl. $R_3$—H is an alkane liquid at reaction conditions, preferably 5 to 12 carbon atoms, most preferably cycloheptane or cyclooctane.

The reaction of step (a) should be carried out at sufficiently high temperature to thermally decompose the alkylhydridometal complex starting material, for example, from 100° to 200° C., preferably 100° to 150° C., most preferably 140° to 150° C. Pressure elevated above atmospheric is also preferred, e.g., 2 to 20 atmospheres. Normally the alkylhydridometal complex starting material should be dissolved in a large excess of the alkane solvent.

Step (b) $CpIr[P(R_1)_3]HMe$+halogenating agent→$CpIr[P(R_1)_3]MeX$

In this step, the methyl complex formed in step (a) is reacted with an organic halogenating agent such as a polyhalogented methane or a haloform of the formulas $CX'X''X'''X''''$ or $CHX'X''X'''$ where $X'$, $X''$, $X'''$, and $X''''$ represent halogen atoms; for example, $CBrCl_3$, $CHBrCl_2$, etc. Although the halogens can be bromine, iodine, or chlorine, bromine is preferred based on overall considerations. The reaction can be carried out, for example, at a temperature in the range of about 0° to 100° C. and a pressure of about 0.5 to 5 atmospheres, with ambient temperature and pressure being preferred for obvious reasons.

The preferred haloform, bromoform, can be conveniently added to the organo-metal complex by adding the neat liquid to a liquid bath or column of the complex to form halogenated product of the formula:

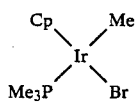

Step (c) CpIr[P(R₁)₃]MeX+HgX'₂→HgMeX+

CpIr[P(R₁)

To remove the methyl group the halogenated methyl complex is reacted with a mercuric halide preferably at ambient conditions to form mercuric methyl halide and a dihalogenated metal complex. The mercuric halide can be HgCl₂, HgBr₂ or HgI₂, with HgCl₂ preferred.

The mercuric methyl halide is next reacted with halogen (i.e., Br₂, a liquid at ambient; I₂, a solid at ambient; or Cl₂, a gas at ambient), preferably bromine, in the form of a liquid to generate the desired alkyl bromide product (or other halide corresponding to the reactants used). This reaction can be carried out by adding the halogen to the complex at a suitable temperature, e.g., 0° to 100° C. at a pressure of 0.5 to 5 atmospheres, preferably at ambient temperature and pressure.

Also formed is a dihalo-counterpart of the starting hydridoalkyl complex. This can be reused by regeneration through reaction of the by-product organo-metal complex, e.g., at ambient condition, with a known hydride source such as lithium aluminum hydride, lithium-triethylborohydride, sodium borohydride, sodium bis-methoxy ethoxy aluminum hydride (commercially available as Red-Al from Aldrich Chemical Company). The resulting organo-metal dihydride can be converted to the organo-metal alkyl complex as described in the above-referenced article in J. Am. Chem. Soc. (1983), 105, pp. 3929-3939.

Step (d) HgMeX'+X''₂=HgX'X''+MeX''

To produce the desired alkyl halide, the mercuric methyl halide is reacted with elemental halogen, preferably I₂ to produce, methyl halide. The reaction condition temperature can be from about 0° to 100° C. at about 0.5 to 5 atmospheres, and is preferably carried out at ambient temperature and pressure.

The following example is illustrative of the present invention, and is not to be regarded as limiting its scope.

EXAMPLE I

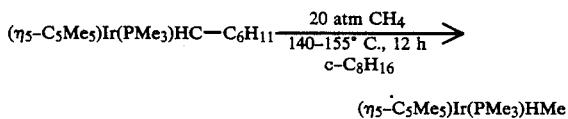

($\eta_5$-C₅Me₅)Ir(PMe₃)HMe

In a Vacuum Atmospheres recirculating inert atmosphere (N₂) box, ($\eta^5$-pentamethylcyclopentadienyl)-(trimethylphosphine)hydridocyclohexyliridium (16.5 mg, 34 μmol) was dissolved in 2 ml anhydrous deoxygenated cyclooctane and transferred to a 20 ml medium-walled pyrex vessel sealed with a vacuum stopcock. The vessel was removed to a vacuum line and degassed through three freeze/pump/thaw cycles. To this solution was added methane (560 torr in a 510 ml known volume bulb) by condensation at −196° C. The sealed vessel was warmed to room temperature behind a blast shield, and then heated in an oil bath for 12 hours at 143° C. and an additional 2 hours at 155° C. The reaction mixture was cooled first to room temperature, then to −196° C., and reconnected to the vacuum line. Following removal of the methane in vacuo at this temperature, the vessel was warmed to room temperature and the volatile materials removed by vacuum transfer. The crude product contained a 58% yield of ($\eta^5$-pentame-thylcyclopentadienyl)(trimethylphosphine)hydridome-thyliridium (determined by ¹H NMR integration against hexamethyldisiloxane internal standard).

If desired, crude material could be purified by low-temperature chromatography on alumina (III) under inert atmosphere (5% diethyl ether in hexane eluent) followed by crystallization from concentrated pentane/hexamethyldisiloxane solution at −40° C. The purified material would have the following analysis: ¹H NMR (C₆D₆): δ 1.87 (d, $J_{PH}$=1.5, 15H, C₅Me₅); 1.22 (d, $J_{PH}$=10.0, 9H, PMe₃); 0.70 (d, $J_{PH}$=6.0, 3H, Ir-CH₃); −17.23 (d, $J_{PH}$=37.9, 1H, Ir-H). ¹³C NMR (C₆D₆): δ 91.1 (d, $J_{PC}$=3.9, C₅Me₅); 19.0 (dq, $J_{PC}$=36.3, $J_{CH}$=127.3, PMe₃); 10.1 (q, $J_{CH}$=126.3, C₅Me₅); 1.38 (q, $J_{CH}$=117.7, Ir-CH₃). IR (C₆D₆): $\gamma_{Ir-H}$ 2090 cm⁻¹. Anal. Calc. for C₁₄H₂₈IrP: C 40.08, H 6.73. Found C 39.68, H, 6.46.

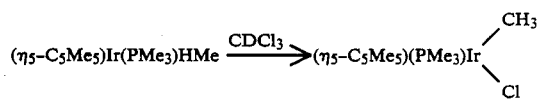

To the crude product from the above experiment dissolved in dry, deoxygenated benzene-d₆ (0.7 ml), was added dry deoxygenated chloroform-d (0.15 ml). After standing overnight at room temperature, the volatile materials were removed under reduced pressure. The residue was purified in the inert atmosphere box by flash chromatography on silica gel (1:1 diethyl ether-hexane eluent), affording ($\eta^5$-pentamethylcyclopentadienyl)-(trimethylphosphine)chloromethyliridium (7.7 mg, 17 μmol, 50% overall yield). The material had the following analysis: ¹H NMR (C₆D₆): δ 1.47 (d, $J_{PH}$=1.9, 15H, C₅Me₅); 1.17 (d, $J_{PH}$=10.3, 9H, PMe₃); 1.08 (d, $J_{PH}$=7.0, 3H, Ir-CH₃). ¹³C NMR (C₆D₆): δ 90.86 (d, $J_{PC}$=3.8, C₅Me₅); 13.88 (d, $J_{PC}$=37.2, PMe₃); 8.87 (s, C₅Me₅); −18.09 (d, $J_{PC}$=10.9, Ir-CH₃). Exact mass: three resolvable isotopomers for C₁₄H₂₇ClPIr M+: Calc. 456.1139, 454.1160 (weighted average of two peaks), 452.1145; Found 456.1148, 454.1133, 452.1123.

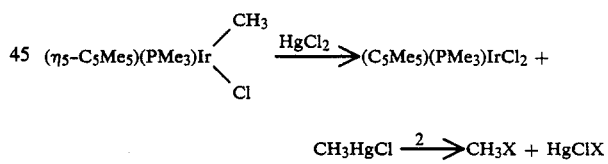

In order to convert ($\eta_5$—C₅Me₅)(PMe₃)Ir(CH₃)Cl to organic halide, 0.025 g of this complex can be dissolved in 30 ml of benzene. After addition of 0.055 g HgCl₂, a precipitate of (C₅Me₅)(PMe₃)IrCl₂ will form within minutes. Filtration will then leave a solution of CH₃HgCl in benzene. Treatment of this solution with 5 μl of Br₂, or 7 μl of I₂, would convert the CH₃HgCl to HgClX (X=Br or I) and a benzene solution of the corresponding methyl halide (CH₃Br or CH₃I), which could be collected by vacuum transfer and quantified by vapor phase chromatography.

The foregoing description of a preferred embodiment of the invention has been presented for purposes of illustration and description. It is not intended to be exhaustive, or to limit the invention to the precise form disclosed, and obviously many modifications and verifications are possible in light of the above teachings. The embodiment was chosen and described in order to best explain the principles of the invention and it practical application to thereby enable others skilled in the art to best utilize the invention in various embodiments and with various modifications as are suited to the particular use contemplated. It is contemplated that embodiments of this invention employing different combinations of reactants will require the use of reaction conditions which may be outside the ranges disclosed herein, but the determination of such appropriate reaction conditions is well within the skill of the art, and in any event such embodiments are contemplated as equivalents of those described and claimed herein. It is intended that the scope of the invention be defined by the claims appended hereto.

What is claimed is:

1. A hydridomethyl complex of the formula:

$$CpIr[P(R_1)_3]HMe$$

wherein Cp represents a cyclopentadienyl or alkyl cyclopentadienyl radical;
 Ir represents an iridium atom;
 P represents a phosphorus atom;
 $R_1$ represents an alkyl group; and
 Me represents a methyl group.

2. The complex of claim 1 wherein $R_1$ represents a methyl or, ethyl, group.

3. The complex of claim 1 wherein $R_1$ represents a methyl group.

4. The complex of claim 1 wherein Cp represents an alkylcyclopentadienyl radial.

5. The complex of claim 1 wherein Cp represents a pentamethylated cyclopentadienyl radical.

6. The complex of claim 4 wherein $R_1$ represents a methyl or, ethyl, group.

7. The complex of claim 5 wherein $R_1$ represents a methyl or, ethyl group.

8. The complex of claim 5 wherein $R_1$ represents a methyl group.

* * * * *

UNITED STATES PATENT AND TRADEMARK OFFICE
CERTIFICATE OF CORRECTION

PATENT NO. : 4,849,534
DATED : July 18, 1989
INVENTOR(S) : Robert G. Bergman et al It is certified that error appears in the above-identified patent and that said Letters Patent is hereby corrected as shown below:

Abstract, last formula, "MeX:" should read --MeX;--.

Signed and Sealed this

Twenty-eighth Day of August, 1990

*Attest:*

HARRY F. MANBECK, JR.

*Attesting Officer*     *Commissioner of Patents and Trademarks*